(12) United States Patent  
Ikeda et al.

(10) Patent No.: US 7,280,860 B2  
(45) Date of Patent: Oct. 9, 2007

(54) NONINVASIVE LIVING BODY MEASURING APPARATUSES

(75) Inventors: Yutaka Ikeda, Kakogawa (JP); Takeo Saitou, Kobe (JP); Rokusaburo Kimura, Kobe (JP); Toshiyuki Ozawa, Miki (JP)

(73) Assignee: Sysmex Corporation, Kobe-shi (JP)

( * ) Notice: Subject to any disclaimer, the term of this patent is extended or adjusted under 35 U.S.C. 154(b) by 324 days.

(21) Appl. No.: 10/778,802

(22) Filed: Feb. 12, 2004

(65) Prior Publication Data

US 2004/0162471 A1     Aug. 19, 2004

(30) Foreign Application Priority Data

Feb. 13, 2003    (JP)   ............................ 2003-035249

(51) Int. Cl.  
*A61B 5/00*      (2006.01)

(52) U.S. Cl. ................. 600/344; 600/310; 600/322

(58) Field of Classification Search ............... 600/309, 600/310, 322, 323, 344  
See application file for complete search history.

(56) References Cited

U.S. PATENT DOCUMENTS

| | | | |
|---|---|---|---|
| 5,090,415 A * | 2/1992 | Yamashita et al. ........... 600/476 |
| 5,228,449 A | 7/1993 | Christ et al. | |
| 5,722,398 A * | 3/1998 | Ishihara et al. ............. 600/322 |
| 5,879,373 A * | 3/1999 | Roper et al. ................. 600/344 |
| 6,061,583 A | 5/2000 | Ishihara et al. | |
| 6,104,939 A | 8/2000 | Groner et al. | |
| 6,240,309 B1 * | 5/2001 | Yamashita et al. ........... 600/407 |
| 6,345,191 B1 * | 2/2002 | Hartmann et al. ........... 600/310 |
| 6,353,750 B1 | 3/2002 | Kimura et al. | |
| 7,139,600 B2 * | 11/2006 | Maki et al. ................. 600/344 |

FOREIGN PATENT DOCUMENTS

| | | |
|---|---|---|
| DE | 43 41 063 A1 | 6/1994 |
| DE | 10043749 A1 | 3/2002 |
| EP | 0 801 297 A1 | 10/1997 |
| EP | 0 917 854 A2 | 5/1999 |
| EP | 0 956 812 A1 | 11/1999 |
| EP | 1 175 864 A2 | 1/2002 |
| WO | WO97/24066 | 7/1997 |
| WO | WO 99/00053 | 1/1999 |
| WO | WO99/00053 | 1/1999 |
| WO | WO 02/071932 A1 | 9/2002 |

* cited by examiner

*Primary Examiner*—Eric Winakur  
*Assistant Examiner*—Etsub D Berhanu  
(74) *Attorney, Agent, or Firm*—Brinks Hofer Gilson & Lione; Gregory H. Zayia

(57) ABSTRACT

Noninvasive living body measuring apparatuses are described, a representative one of which includes: (a) a light source unit for irradiating a measurement region of a living body; (b) a light-receiving unit for detecting optical information from an irradiated measurement region; (c) a first holding unit for holding the light source unit and the light-receiving unit; (d) a second holding unit for holding the first holding unit so as to be movable; and (e) a mounting unit for mounting the second holding unit onto a living body.

15 Claims, 10 Drawing Sheets

NONINVASIVE LIVING BODY MEASURING APPARATUSES

FIELD OF THE INVENTION

The present invention relates to noninvasive living body measuring apparatuses.

BACKGROUND

Noninvasive blood analyzers are known (e.g., WO97/24066) that are provided with a light source for irradiating parts of living tissue including blood vessels, an image capturing unit for imaging the irradiated blood vessels and tissue, and an analyzing unit for analyzing the obtained image. The analyzing unit includes an extracting unit for extracting an image density distribution showing a transverse distribution of blood vessels in the obtained image as an image density profile, a quantifying unit for morphologically quantifying the characteristics of the profile, a calculating unit for calculating the quantity of blood components based on the quantified characteristics, an output unit for outputting the calculation results, and living body inspecting apparatuses (e.g., WO99/00053). The living body inspecting apparatuses are provided with a base for positioning a part of a living body used as an examination object, side wall members which can hold the positioned part of the body from two sides, a light source supported by the base and the side wall members for supplying light to the living body, and a light-receiving unit for detecting optical information from the irradiated part of the living body.

Although the above-mentioned noninvasive living body measuring apparatuses are capable of simple transdermal blood analysis and continuous monitoring, it would be desirable to improve the analysis accuracy to a degree comparable to blood analysis by conventional blood sample collection.

In the living body inspection apparatuses described in PCT publications WO 97/24066 and WO 99/00053, since the measurement subject is a peripheral vein in a finger or the like, individual subdermal physiological differences in blood vessels and blood flow conditions in living bodies are the main causes of fluctuation in measurement values. These differences in physiological conditions are considered to be a factor regulating the limit of analysis accuracy.

SUMMARY

The scope of the present invention is defined solely by the appended claims, and is not affected to any degree by the statements within this summary.

A first noninvasive living body measuring apparatus embodying features of the present invention includes: (a) a light source unit for irradiating a measurement region of a living body; (b) a light-receiving unit for detecting optical information from an irradiated measurement region; (c) a first holding unit for holding the light source unit and the light-receiving unit; (d) a second holding unit for holding the first holding unit so as to be movable; and (e) a mounting unit for mounting the second holding unit onto a living body.

A second noninvasive living body measuring apparatus embodying features of the present invention includes: (a) a first light source unit for irradiating a blood vessel; (b) a second light source unit for irradiating tissue of a living body; (c) a first light-receiving unit for detecting optical information from the blood vessel irradiated by the first light source unit; (d) a second light-receiving unit for detecting optical information from the tissue of the living body irradiated by the second light source unit; and (e) an analyzing unit for analyzing a blood component flowing in a blood vessel based on optical information detected by irradiation with the first and second light source units.

A third noninvasive living body measuring apparatus embodying features of the present invention includes: (a) a light source for irradiating a measurement region of a living body; (b) an image capturing optical system for detecting reflected light from an irradiated measurement region; and (c) a light-detecting element for detecting the reflected light from the irradiated measurement region. The light source and the light-detecting element are arranged substantially in a circle centered around a center axis of the image capturing optical system.

DETAILED DESCRIPTION

Figure 1:
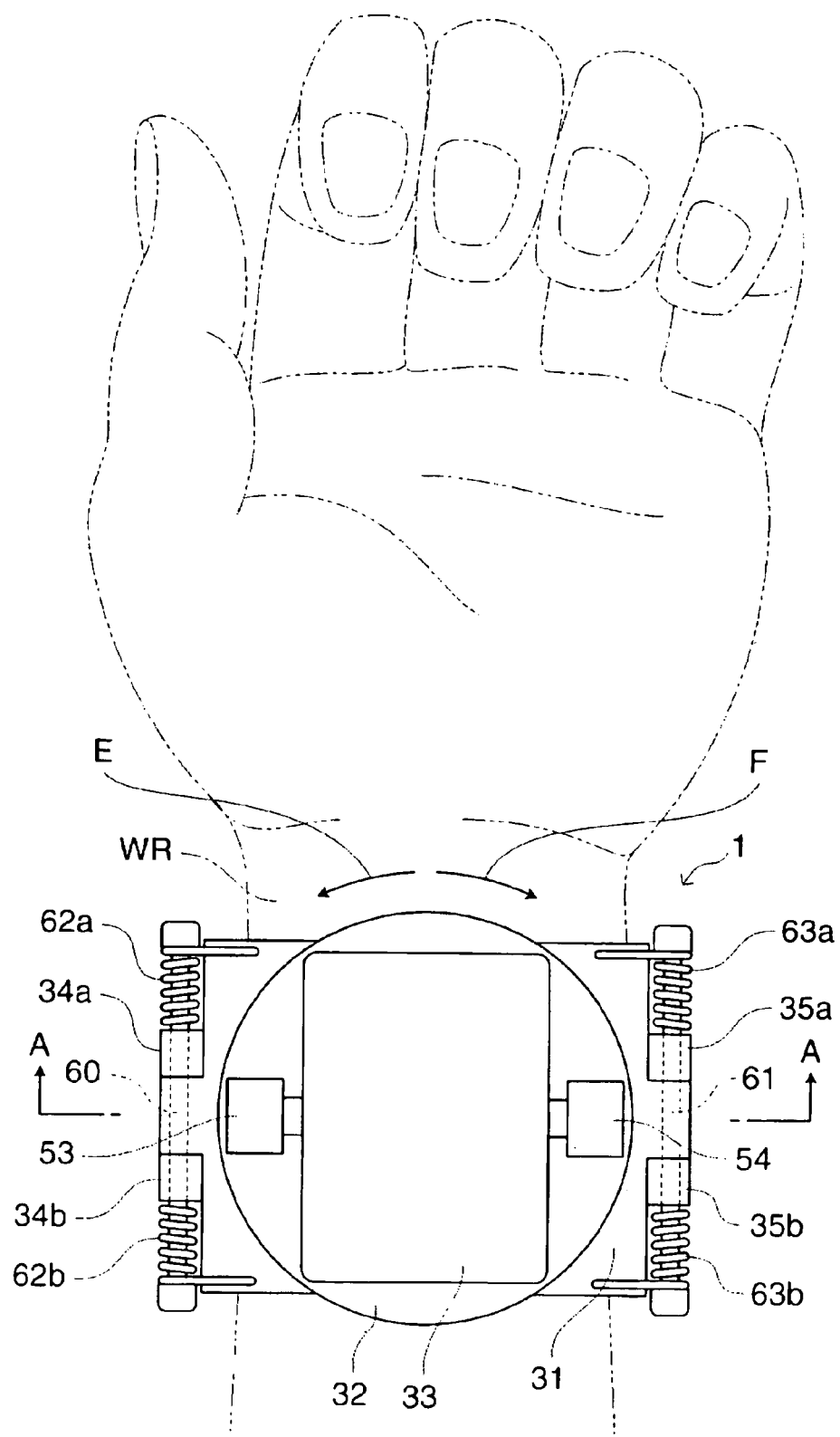
FIG. 1 shows a top view of part of an embodiment of the present invention.

Noninvasive living body measuring apparatuses, which improve analysis accuracy, have been discovered and are described below.

The present invention provides a noninvasive living body measuring apparatus including a light source for irradiating the measurement region of a living body, a light-receiving unit for detecting optical information from the irradiated measurement region, a first holding unit for holding the light source and the light-receiving unit, a second holding unit for holding the first holding unit so as to be movable, and a mounting unit for mounting the second holding unit onto a living body.

As used herein, the phrase "living body" refers without limitation to any mammalian animal, including but not limited to a human being, rabbit, dog, cat, rat, mouse, and the like. In addition, as used herein, the phrase "part of a living body" does not refer to tissue separated from the living body, but rather to an integral part of the tissue of the living body, for example, a finger, toe, sole of a foot, or neck in the case of a human being.

In accordance with the present invention, it is presently desirable that the mounting unit elastically anchors part of the living body at a suitable pressure using the second holding unit. This arrangement is used because when the second holding unit anchors a part of a living body by means of a rather strong pressure, the blood vessels are compressed so as to produce a congestive condition and ischemic condition, such that accurate inspection results cannot be obtained.

A light source such as a semiconductor laser (hereinafter referred to as LD), LED or halogen light source may be used as the light source in accordance with the present invention, and the light source may irradiate part of the living body directly or through an optical fiber. It is presently desirable that the wavelength of the irradiating light is in the range of about 400 to about 950 nm.

The light-receiving unit may include a photoreceptor element such as a photodiode, CCD, and the like. The light-receiving unit may also include an optical system such as a lens and the like.

The first holding unit may be rotatable relative to the second holding unit.

The light source unit may be provided with a light source for irradiating a desired blood vessel in the measurement region.

The light source unit may be provided with a light source for illuminating tissue of the living body in the measurement region.

The mounting unit may be provided with a holding member capable of holding a part of the living body.

The light-receiving unit may be provided with an image capturing element for capturing the measurement region.

The light-receiving unit may be provided with a photosensor element for detecting the light received from the tissue of the measurement region.

The analyzing unit may be a microcomputer, personal computer or the like.

In another aspect, the present invention provides a non-invasive living body measuring apparatus including: a first light source unit for irradiating blood vessels; a second light source unit for irradiating tissue of a living body; a first light-receiving unit for detecting optical information from a blood vessel irradiated by the first light source unit; a second light-receiving unit for detecting optical information from tissue of the living body irradiated by the second light source unit; and an analysis unit for analyzing a blood component flowing in the blood vessel based on optical information detected by means of the respective irradiation by the first and second light source units.

The light-receiving unit may be provided with an image capturing element for capturing the image of a blood vessel irradiated by the first light source unit, and a photosensor element for detecting the light received from the tissue irradiated by the second light source unit.

The analyzing unit may be provided with a calculating unit for calculating the amount of a blood component based on the captured image, and the calculating unit may correct the amount of blood component based on the optical information obtained from the photosensor element.

The first light source unit may include first and second light sources for irradiating a blood vessel interposed therebetween. The second light source unit may include third and fourth light sources at mutually different distances from the photosensor element to a part of the living body. The image capturing element may capture a first image of a blood vessel simultaneously irradiated by both the first and second light sources, a second image of a blood vessel irradiated by the first light source, and a third image of a blood vessel irradiated by the second light source. The photosensor element may detect light received from the tissue of the living body irradiated by the third light source, and may detect the amount of light received from the tissue of the living body irradiated by the fourth light source.

The analyzing unit may be provided with a calculating unit for calculating the amount of a blood component based on the obtained first, second, and third images, and the calculating unit may determine the reliability of this blood component amount based on characteristics of the second and third images, and on each amount of light obtained during irradiation by the third and fourth light sources. The calculating unit may also correct the blood component amount based on each amount of light obtained during irradiation by the third and fourth light sources.

One method for improving analysis accuracy embodying features of the present invention is to not use as a target of measurement those parts of the living body, such as peripheral veins, which are readily affected by physiological factors, but rather to use veins which are farther downstream (i.e., nearer the heart) and therefore less easily influenced by physiological factors.

Presently preferred embodiments in accordance with the present invention will now be described in reference to the appended drawings. It is to be understood that these drawings and their accompanying descriptions are provided solely by way of illustration and that the present invention is not limited thereby.

Figure 13:
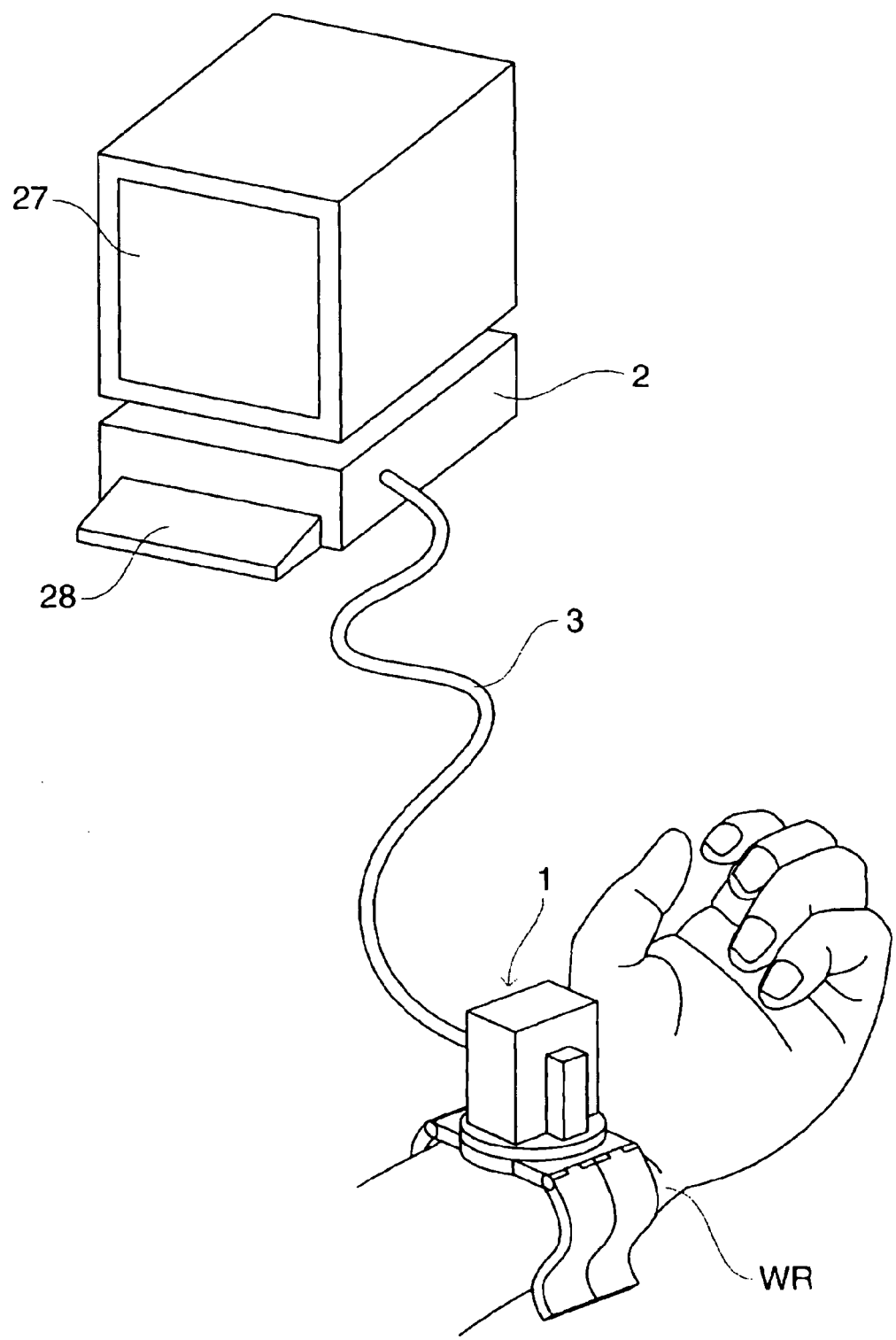
FIG. 13 shows a perspective view of an embodiment of the present invention.

FIG. 13 is a perspective view showing an example of the structure of an embodiment of the present invention. A detecting unit 1 is mounted on a human wrist WR, and the detecting unit 1 is connected to an analyzing unit 2 by means of a cable 3. An input unit 28 is connected to the analyzing unit 2. Information from the detecting unit 1 is output to an output unit 27 through the analyzing unit 2.

FIG. 1 is a top view of the detecting unit 1 mounted on a human wrist WR.

Figure 2:
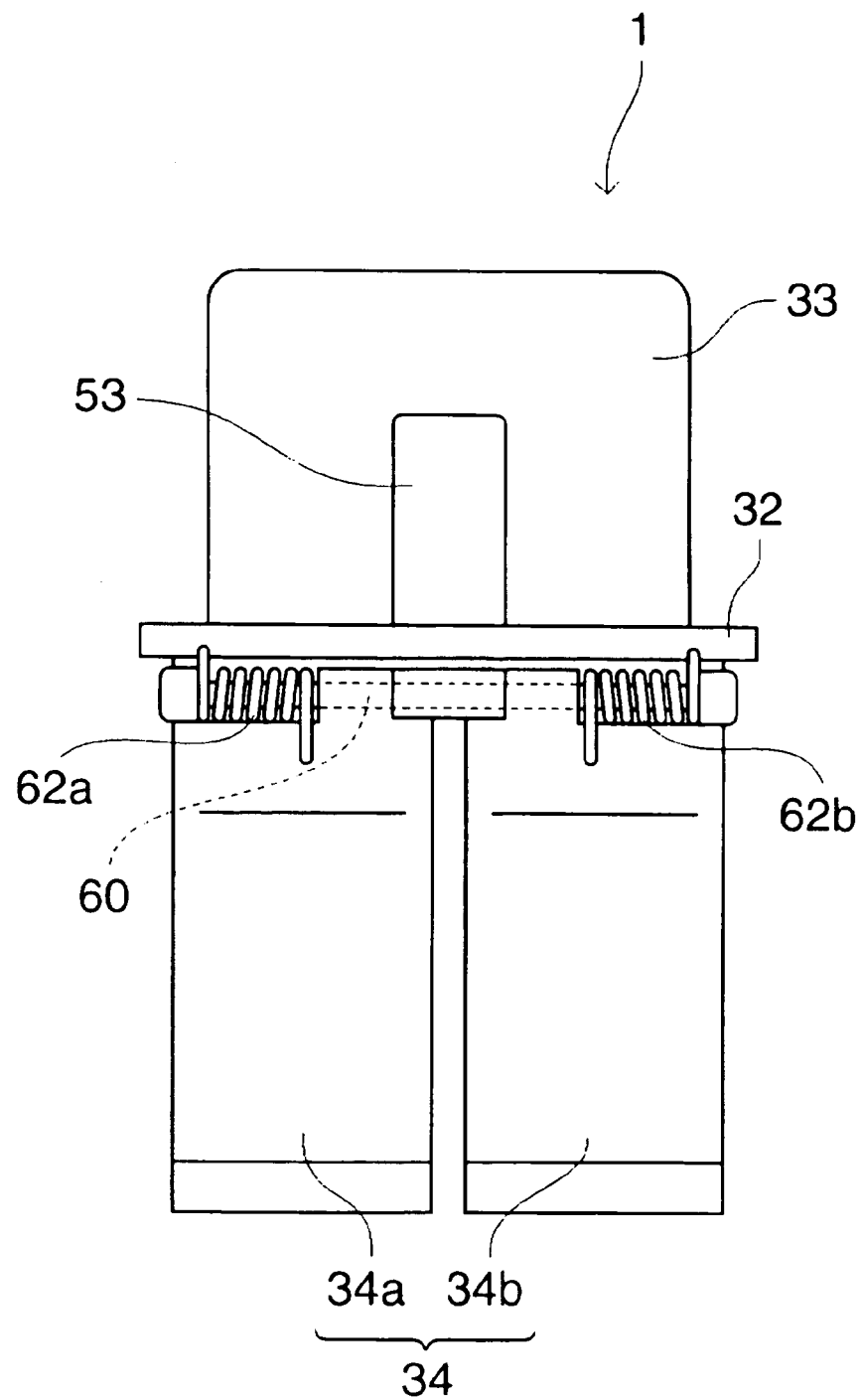
FIG. 2 shows a side view of part of an embodiment of the present invention.
Figure 3:
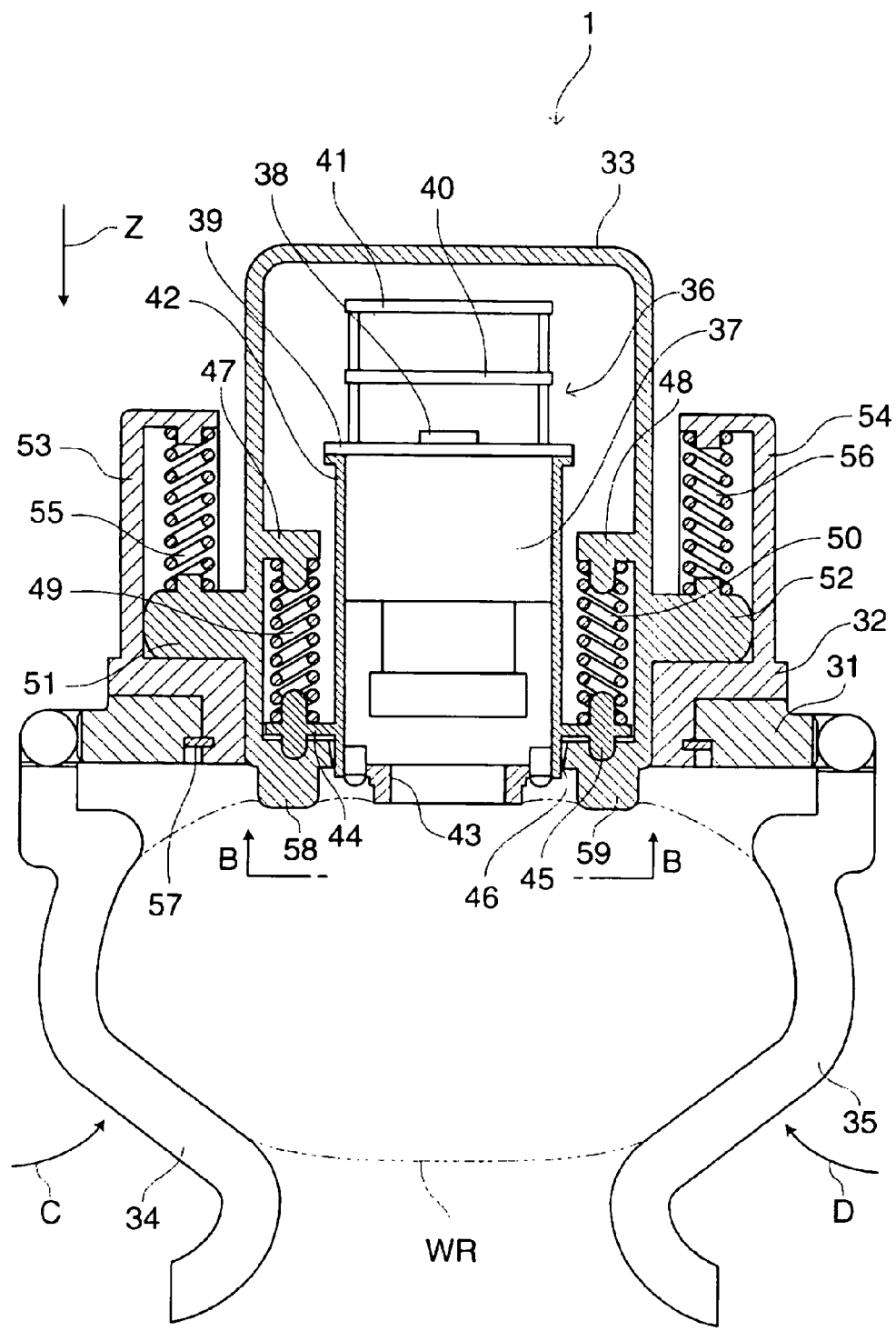
FIG. 3 shows a cross-sectional view taken along the line A-A in FIG. 1.
Figure 4:
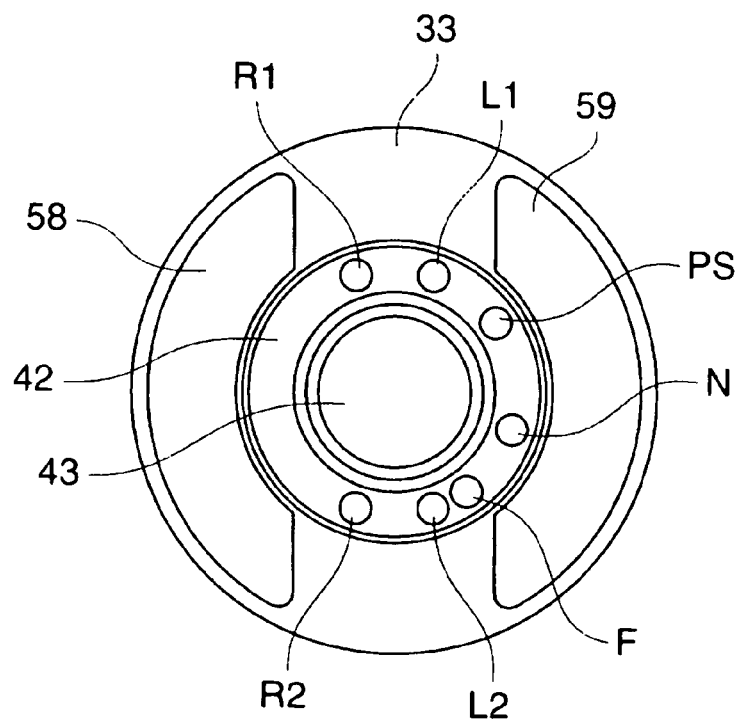
FIG. 4 shows a cross-sectional view taken along the line B-B in FIG. 3.

FIG. 2 is a side view of the detecting unit 1. FIG. 3 is a cross-sectional view along the A-A arrow line of FIG. 1, and FIG. 4 is a view along the B-B arrow line of FIG. 3.

As shown in these drawings, the detecting unit 1 is provided with a support base 31, a rotating base 32 inserted perpendicularly into a center opening of the support base 31 so as to be rotatable in the arrow E and arrow F directions (FIG. 1), a housing 33 installed at the center opening of the rotating base 32, and a pair of grippers 34 and 35 for holding the wrist WR on the support base 31.

As shown in FIG. 3, the bottom of the housing 33 is provided with an opening 46, and accommodates an image capturing unit 36 within. The image capturing unit 36 is provided with a cylindrical lens barrel 37 accommodating an objective lens, a substrate 39 on which is mounted a CCD image capturing element 38, and substrates 40 and 41 on which are mounted electronic components for driving the CCD image capturing element 38. The image capturing unit 36 is supported by being perpendicularly inserted into a cylindrically shaped support member 42.

The bottom of the support member 42 has a round opening 43. Six light-emitting diodes, R1, R2, L1, L2, N, and F, and a single photosensor PS are arranged on the circumference of a circle around the opening 43 and having the same center as the opening 43, as shown in FIG. 4. The support member 42 has a pair of fasteners 44 and 45 protruding horizontally from the bottom end outer wall. The fasteners 44 and 45 fasten to the bottom peripheral edge of the housing 33 such that the opening 43 extends downward from the opening 46 on the bottom of the housing 33.

The housing 33 is provided with a pair of projections 47 and 48 which extend horizontally from the inner wall surface, and are connected by the respective compression springs 49 and 50 between the projection 47 and fastener 44, and between the projection 48 and the fastener 45. The springs 49 and 50 exert a force on the fasteners 44 and 45, respectively, in the arrow Z direction.

The housing 33 has a pair of fasteners 51 and 52 extending horizontally from the outer wall surface. The fasteners 51 and 52 fasten to the edge of the opening on the rotating base 32. The top surface of the rotating base 32 has a pair of spring receptacles 53 and 54, and these spring receptacles 53 and 54 accommodate the compression springs 55 and 56 which exert a force on the fasteners 51 and 52, respectively, in the arrow Z direction.

A ring-like elastic member 57 is mounted on the interface between the rotating base 32 and the inner surface of the opening of the support base 31. The elastic member 57 functions to prevent the rotating base 32 from detaching upward from the support base 31, and functions as a friction member for exerting a suitable friction force between the rotating base 32 and the support base 31 while the rotating base 32 is rotating.

The housing 33 is provided with a pair of projections 58 and 59 which extend downwardly from the edge of the opening 46. These projections 58 and 59 contact the surface of the wrist WR, so as to press against the surface of the wrist WR with a suitable pressure exerted by the elasticity of the springs 55 and 56. Furthermore, the opening 43 also contacts the surface of the wrist WR so as to press against the surface of the wrist WR with a suitable pressure exerted by the elasticity of the springs 49 and 50. In this way, the projections 58 and 59 and the opening 43 contact the surface of the wrist WR without compressing the blood vessels.

As shown in FIG. 2, the gripper 34 is divided into segments 34a and 34b, and pivots about the support base 31 via a through-pin 60. The pin 60 is provided with springs 62a and 62b which exert a force on the segments 34a and 34b, respectively, in the arrow C direction (FIG. 3).

The gripper 35 is similarly divided into segments 35a and 35b (FIG. 1), and pivots on the support base 31 via a through-pin 61. The pin 61 is provided with springs 63a and 63b which exert a force on the segments 35a and 35b, respectively, in the arrow D direction (FIG. 3).

The springs 62a, 62b, 63a, and 63b exert a force on segments 34a, 34b, 35a, and 35b which is sufficient to reliably anchor the wrist WR on the support base 31. Furthermore, since the grippers 34 and 35 are each divided into two segments, the support base 31 can be stably mounted onto the wrist WR even though a protuberance (wrist bone) is present at the mounting site.

The optical axis of the objective lens housed in the lens barrel 37, the center axis of the circular opening 43, and the rotation axis of the rotating base 32 are mutually aligned.

Figure 6:
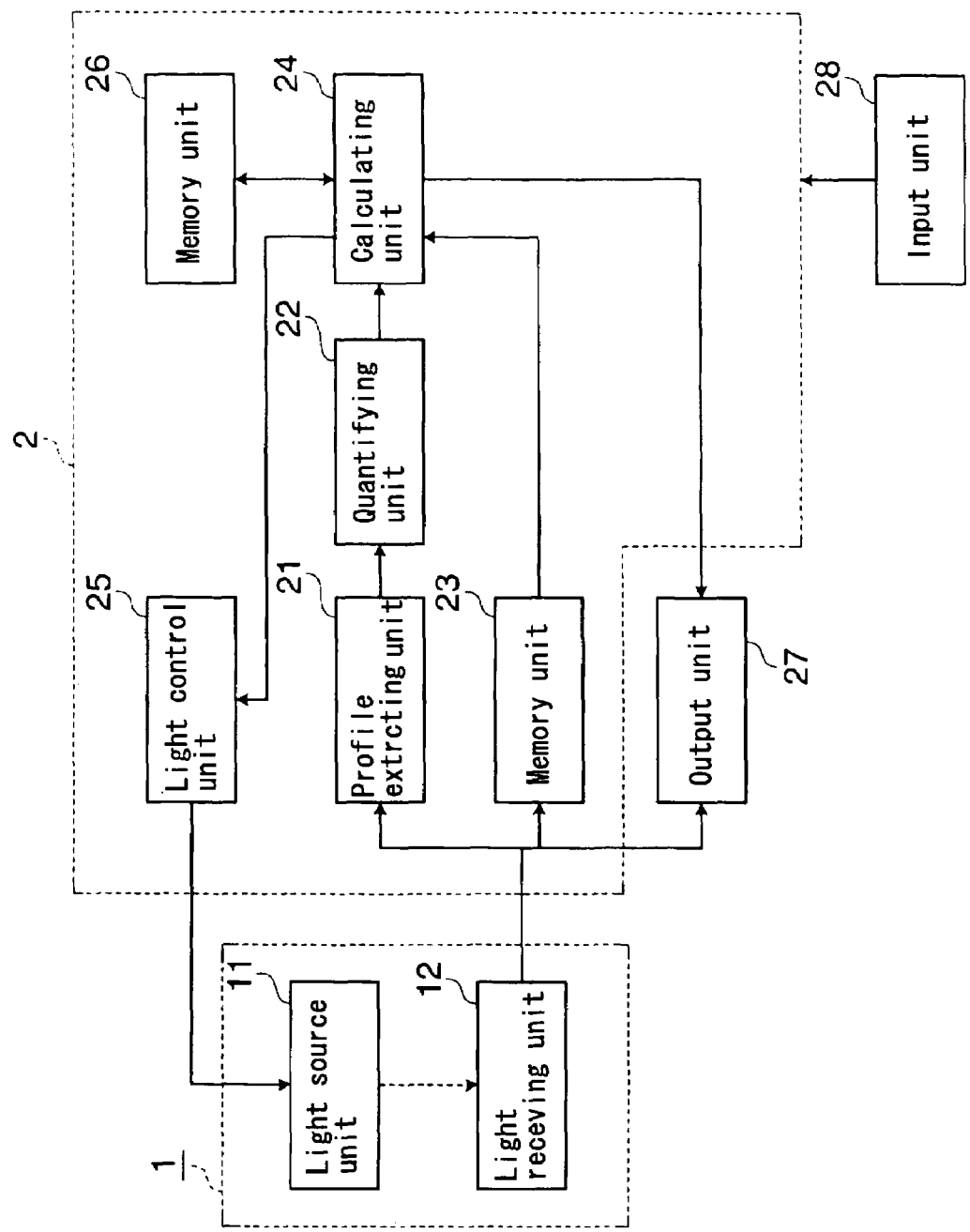
FIG. 6 shows a block diagram of the structure of an embodiment of the present invention.

FIG. 6 is a block diagram showing the structure of a noninvasive living body measuring apparatus embodying features of the present invention.

The living body measuring apparatus shown in the drawing includes a detecting unit 1, analyzing unit 2, and input unit 28. The detecting unit 1 includes a light source unit 11 and light-receiving unit 12. The light source unit 11 is provided with six light-emitting diodes R1, R2, L1, L2, N, and F (FIG. 4), and the light-receiving unit 12 is provided with a CCD image capturing element 38 (FIG. 3) and a photosensor PS (FIG. 4).

Figure 5:
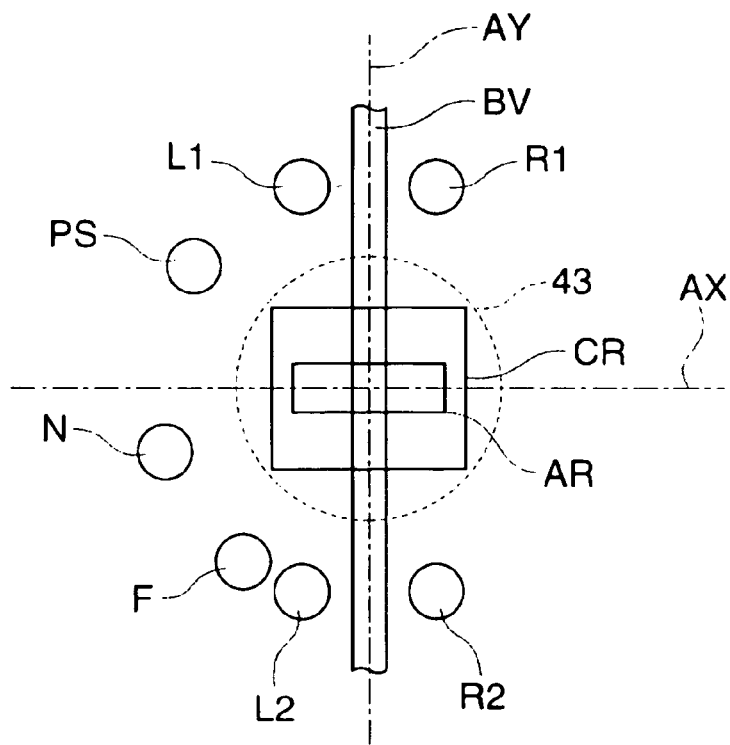
FIG. 5 shows an illustration of part of a living body arranged in accordance with an embodiment of the present invention.

When the detecting unit 1 is mounted on a human wrist WR as shown in FIG. 1, a measurement region is circumscribed by the light-emitting diodes R1, R2, L1, L2, N, and F, as shown in FIG. 5. The light-emitting diodes R1, R2, L1, and L2 are arranged symmetrically on a first axis AY and second axis AX which mutually intersect through the center of the opening 43. The light-emitting diodes R1, R2, L1, and L2 irradiate a blood vessel BV from both sides, and the light-emitting diodes N and F irradiate an area that does not include the blood vessel BV. Then, the CCD image capturing element 38 captures the optical image (in this case, a reflected optical image) of the image capturing region CR which includes the irradiated blood vessel BV. The photosensor PS measures the amount of light from the light emitting diodes N and F that passes through the living body part, which does not include the blood vessel BV, and enters the photosensor. The light-emitting diode N is provided closer to the photosensor PS than is the light-emitting diode F.

A profile extracting unit 21 extracts the image density distribution of the analysis region AR (FIG. 5) of the image captured by the CCD image capturing element 38 of the light-receiving unit 12 as a luminance profile. A quantifying unit 22 quantifies the morphological characteristics of the extracted luminance profile. A memory unit 23 converts and stores the optical information obtained by the light-receiving unit 12 as digital data.

A calculating unit 24 calculates the blood component concentration and the like based on the light quantity data and the quantified characteristics. A light control unit 25 performs suitable feedback control based on information obtained from the light-receiving unit 12, which receives the light from the light source unit 11. The memory unit 26 stores the results calculated by the calculation unit 24. An output unit 27 outputs the calculation result and a monitor image. An input unit 28 includes a mouse and keyboard, and is used to input settings for measurement conditions and calculation conditions.

Figure 7:
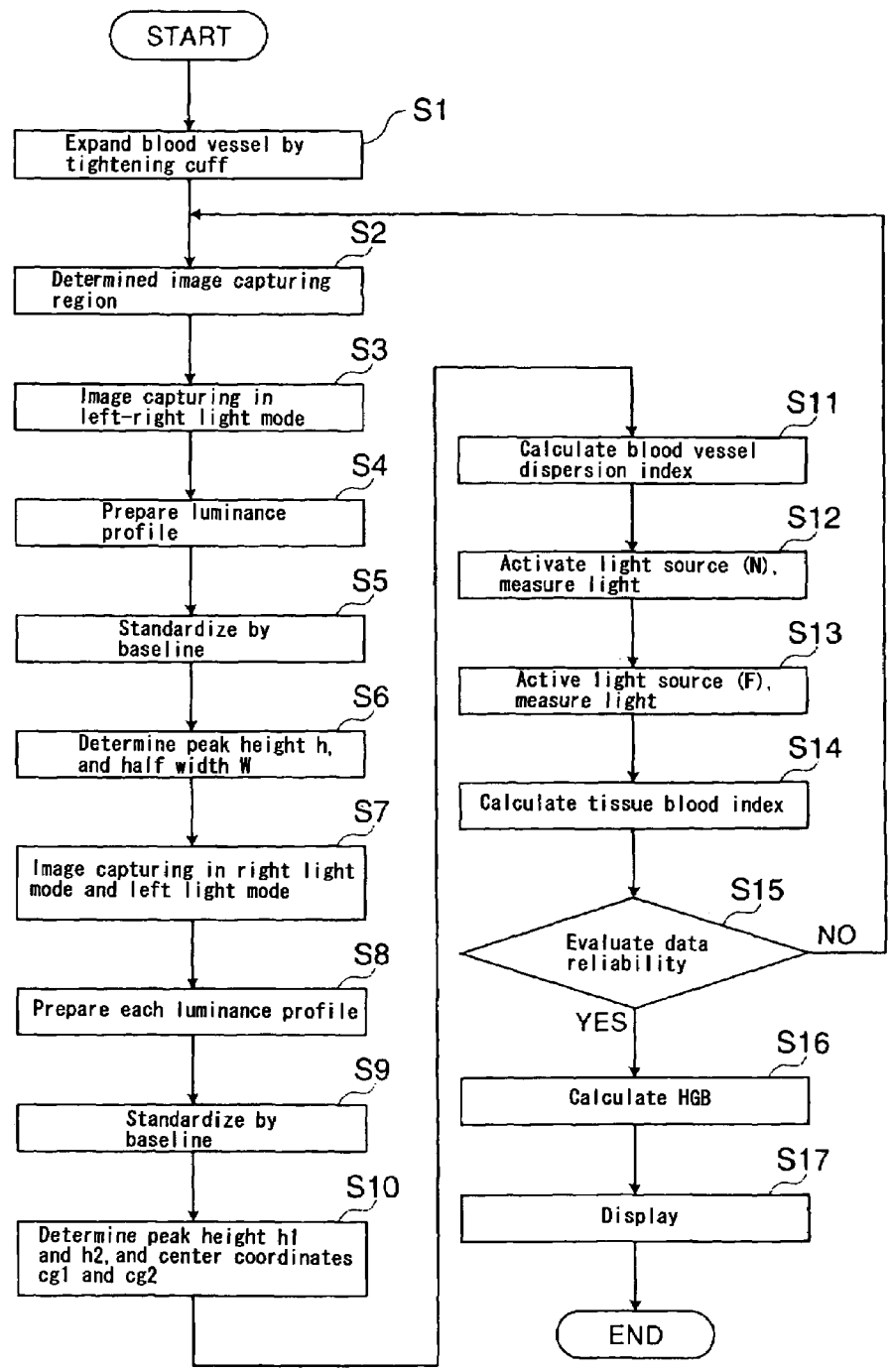
FIG. 7 shows a flow chart of the operation of an embodiment of the present invention.

The measurement operation performed by an apparatus having the above-described structure is described below in reference to the flow chart shown in FIG. 7.

First, the arm of a subject was wrapped with a cuff (blood pressure measuring band, not shown). The pressure is increased until blood flow in the wrist is impaired and the blood vessels (veins) in the wrist are expanded. The detecting unit 1 is mounted on the wrist as shown in FIG. 1, and the position of the measurement region is adjusted (S1 and S2). In this case, while viewing a monitor image output from the output unit 27, the housing 33 is rotated in the arrows E and F directions (FIG. 1) to adjust the position of the image capturing region CR, such that the blood vessel BV is disposed between the light-emitting diodes R1 and L1 and between the light-emitting diodes R2 and L2, as shown in FIG. 5.

When the input unit 28 provides an instruction to start the measurement, the light control unit 25 and the light source unit 11 irradiate a suitable amount of light by the light-emitting diodes R1, R2, L1, and L2 (left-to-right lighting mode) on the measurement region of part of a living body (in this case, a human wrist) including a blood vessel BV. The image capturing region CR is captured by the CCD image capturing element 38. In this way, an image of the tissue is obtained which includes an image of the blood vessel (vein) BV within the image capturing region CR (S3).

Figure 8:
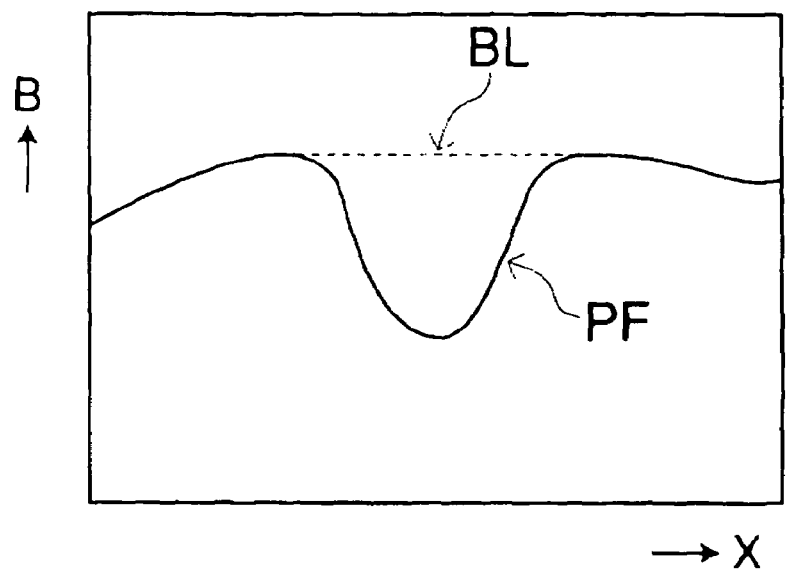
FIG. 8 shows an illustration of the imaging process of an embodiment of the present invention.

Next, the profile extracting unit 21 prepares a luminance profile (distribution of luminance B relative to position X) PF transversing the blood vessel BV within the analysis region AR (FIG. 5), as shown in FIG. 8. The noise component is reduced using a method such as Fast Fourier Transformation or the like (S4).

Figure 9:
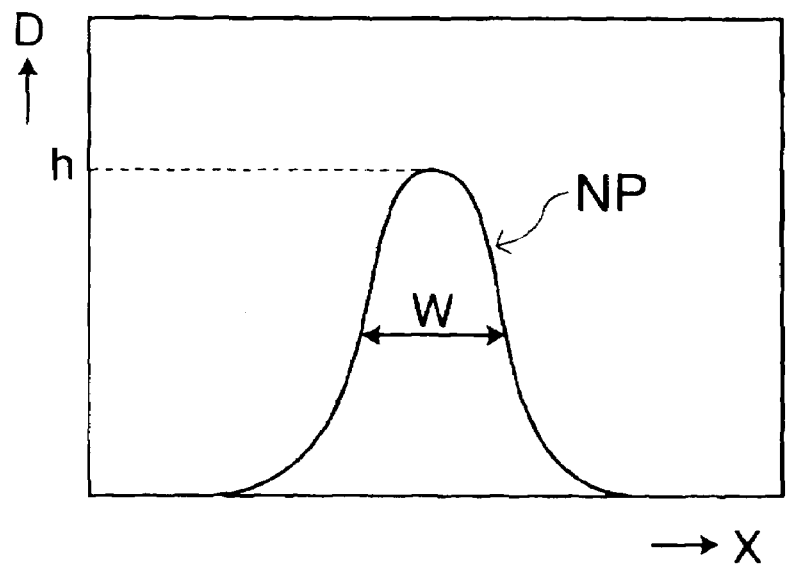
FIG. 9 shows an illustration of the imaging process of an embodiment of the present invention.

The quantifying unit 22 standardizes the luminance profile PF obtained in S4 using a baseline BL (FIG. 8). The baseline BL basically determines the shape of the luminance profile PF of the part absorbed by the blood vessel. In this way, a luminance profile (distribution of density D relative to position X) NP is obtained which does not include incidence light, as shown in FIG. 9 (S5).

The calculating unit 24 calculates a peak height h and half width w for the standardized luminance profile NP. The obtained value h represents the ratio of the light intensity absorbed by the blood vessel (blood) and the light intensity passed through the tissue area of the measurement object. The value w represents a length equivalent to the blood vessel diameter (S6).

Figure 10:
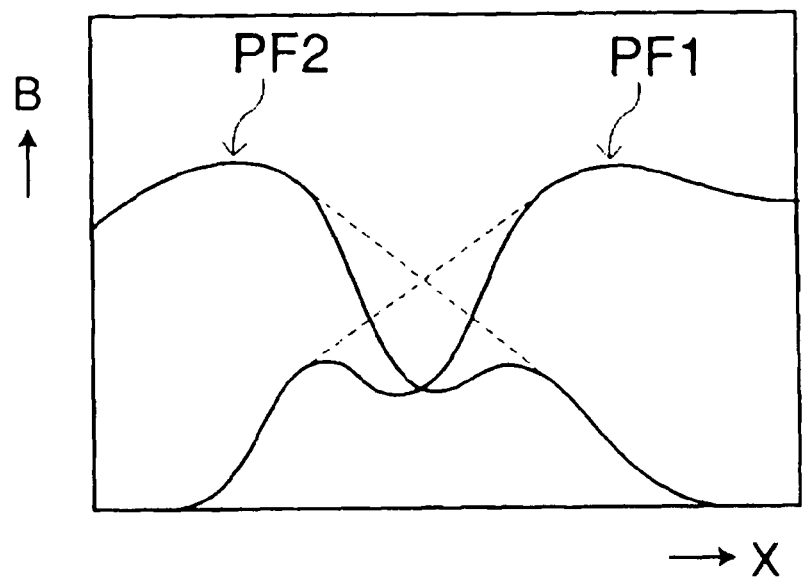
FIG. 10 shows an illustration of the imaging process of an embodiment of the present invention.
Figure 11:
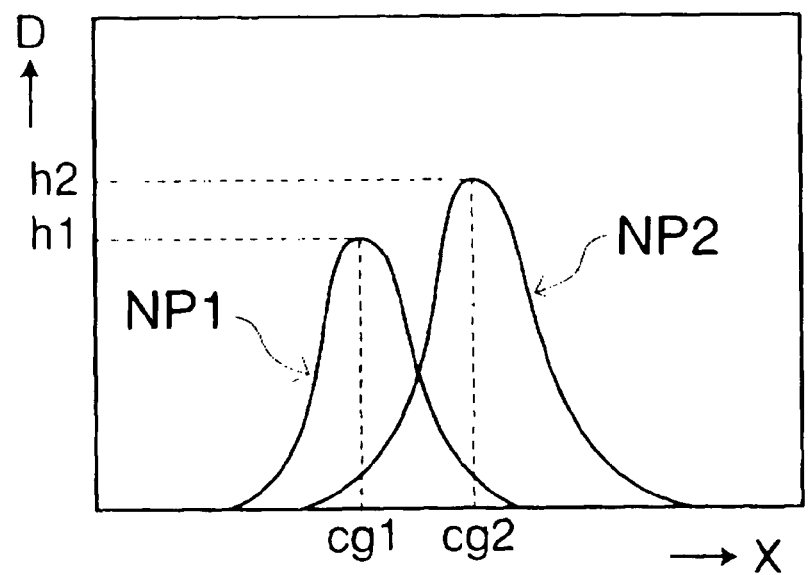
FIG. 11 shows an illustration of the imaging process of an embodiment of the present invention.

The same part that was imaged in S3 is irradiated by a suitable amount of light by the light-emitting diodes R1 and R2 (right light mode), and the area is imaged. Then, the area is irradiated by a suitable amount of light by the light-emitting diodes L1 and L2 (left light mode), and the area is imaged (S7). Next, the respective images obtained in S7 are processed by the profile extracting unit 21 using the same process as in S4 to obtain luminance profiles PF1 and PF2, as shown in FIG. 10 (S8).

The luminance profiles PF1 and PF2 obtained in S8 are processed by the quantifying unit 22 using the same process as in S5 to obtain luminance profiles NP1 and NP2 which do not include incidence light (S9).

The calculating unit 24 respectively calculates the peak height h1 and center coordinate cg1 from the luminance profile NP1 obtained by irradiation by light-emitting diodes R1 and R2, and calculates the peak height h2 and center coordinate cg2 from the luminance profile NP2 obtained by irradiation by the light-emitting diodes L1 and L2 (S10).

Then, the calculating unit 24 calculates the blood vessel dispersion index S, based on the following equation, using the results obtained in S10 (S11).

$$S = (cg2 - cg1)/[(h1 + h2) \cdot 2] \quad (1)$$

The light control unit 25 and the light source unit 11 irradiate the part of the living body near the image capturing region CR using the light-emitting diode N and a suitable amount of light. The amount of light v1 entering the photosensor PS through the part of the living body is measured. The measurement result is stored in the memory unit 23 (S12).

The light control unit 25 and the light source unit 11 activate the light-emitting diode F to emit an amount of light identical to the light emitted by the light-emitting diode N in S12. The amount of light v2 entering the photosensor PS is measured and stored in the same manner as in S12 (S13).

The calculating unit 24 calculates the tissue blood index D, based on the following equation, using the results obtained in S12 and S13 (S14).

$$D = \log(v1/v2) \quad (2)$$

The calculating unit 24 determines whether or not the blood vessel dispersion index S obtained in S11 and the tissue blood index D obtained in S14 satisfy the following condition (S15).

$$a1 \cdot S^b \leq D \leq a2 \cdot S^b \quad (3)$$

(Where a1<a2, and a1, a2, and b are constants determined experimentally.)

When the condition of equation (3) is not satisfied, the reliability of the measurement result is deemed low, and either re-measurement is performed or measurement is stopped. When the condition of equation (3) is satisfied, the reliability of the measurement result is deemed high, and the routine continues to S16.

The calculating unit 24 determines the correction ratio using D and a correction calibration curve determined experimentally. The blood concentration within the blood vessel is calculated from the values h and w to approximate the Lambert-Berr's law, and this result is multiplied by the correction ratio as the hemoglobin concentration HGB, and stored in the memory unit 23 (S16). Then, the captured image, each density profile, the calculated HGB, and the like are displayed on the output unit 27 (S17).

Thus, the hemoglobin concentration in the blood of the subject can be measured in this way.

Figure 12:
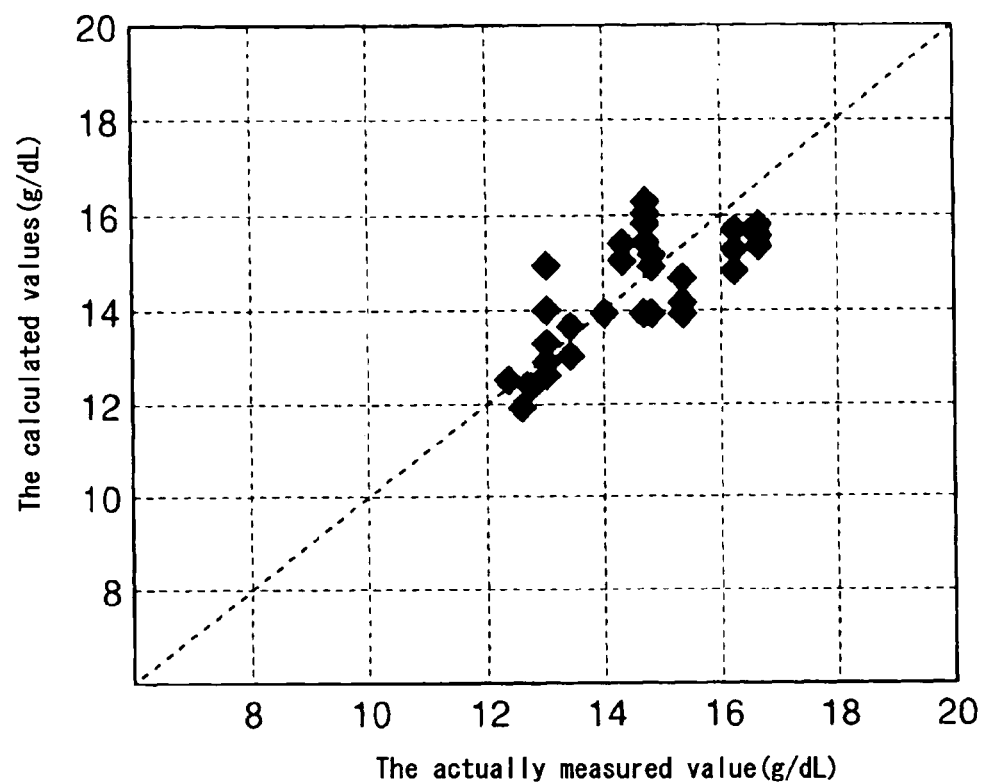
FIG. 12 shows a graph of the degree of matching of actual measurement values and calculated values.

FIG. 12 is a graph plotting the calculated values of the measuring apparatus of the present invention and the actually measured values obtained from a hemocytometer and the like. This graph clearly shows that the measuring apparatus of the present invention can measure hemoglobin concentration with high precision.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A noninvasive living body measuring apparatus comprising:
   a light source unit for irradiating a measurement region of a living body;
   a light-receiving unit for detecting optical information from an irradiated measurement region;
   a first holding unit for holding the light source unit and the light-receiving unit;
   a second holding unit for holding the first holding unit; and
   a mounting unit for mounting the second holding unit onto the living body;
   wherein the light-receiving unit comprises an objective lens and an image capturing element for capturing an image of the measurement region, and the first holding unit is rotatable around an optical axis of the objective lens when the mounting unit mounts the second holding unit onto the living body.

2. The apparatus of claim 1, wherein the light source unit comprises a first light source for irradiating a blood vessel in the measurement region.

3. The apparatus of claim 2, wherein the light source unit further comprises a second light source for irradiating tissue of the living body in the measurement region.

4. The apparatus of claim 2, further comprising an output unit for displaying optical information from the irradiated measurement region.

5. The apparatus of claim 3, wherein the light-receiving unit comprises a light-detecting element for detecting a light received from the tissue of the living body.

6. The apparatus of claim 1, wherein the mounting unit comprises at least one holder capable of holding the living body.

7. The apparatus of claim 1, wherein the first holding unit comprises an elastic member for elastically holding the light source unit and the light-receiving unit.

8. The apparatus of claim 1, further comprising:
an analyzing unit for analyzing detected optical information; wherein
the analyzing unit comprises a calculating unit for calculating an amount of a blood component based on the captured image.

9. The apparatus of claim 1, wherein the light-receiving unit detects information of light reflected from the irradiated measurement region.

10. A noninvasive living body measuring apparatus comprising:
a first light source unit for irradiating a blood vessel;
a second light source unit for irradiating tissue of a living body;
a first light-receiving unit for detecting optical information from the blood vessel irradiated by the first light source unit;
a second light-receiving unit for detecting optical information from the tissue of the living body irradiated by the second light source unit; and
an analyzing unit for analyzing a blood component flowing in a blood vessel based on optical information detected by irradiation with the first and second light source units;
wherein the first light-receiving unit comprises an image capturing element for capturing an image of the blood vessel irradiated by the first light source unit, and the second light-receiving unit comprises a light-detecting element for detecting light received from the tissue of the living body irradiated by the second light source unit;
wherein the first light source unit comprises first and second light sources for irradiating a blood vessel interposed therebetween, and the second light source unit comprises third and fourth light sources at mutually different distances from the light-detecting element; and
wherein the image capturing element captures a first image of the blood vessel irradiated simultaneously by the first and the second light sources, a second image of the blood vessel irradiated by the first light source, and a third image of the blood vessel irradiated by the second light source, and wherein the light-detecting element detects light received from the tissue of the living body irradiated by the third light source, and light received from the tissue of the living body irradiated by the fourth light source.

11. The apparatus of claim 10, wherein the analyzing unit comprises a calculating unit for calculating an amount of the blood component based on a captured image, and the calculating unit corrects the amount of the blood component based on a detected result from the light-detecting element.

12. The apparatus of claim 10, wherein the analyzing unit comprises a calculating unit for calculating an amount of the blood component based on the first, second, and third images, and the calculating unit determines reliability of the amount of the blood component based on each detected result during irradiation by the third and fourth light sources and on characteristics of the second and third images obtained.

13. The apparatus of claim 10, wherein the analyzing unit comprises a calculating unit for calculating an amount of the blood component based on the first, second, and third images, and the calculating unit corrects the amount of the blood component based on each detected result during irradiation by the third and fourth light sources.

14. A noninvasive living body measuring apparatus comprising:
a plurality of light sources for irradiating a measurement region of a living body;
an image capturing optical system for detecting reflected light from an irradiated measurement region; and
a position adjuster for adjusting a position of the light sources with respect to a blood vessel of the living body;
wherein the plurality of light sources comprises four light sources arranged at respective corners of a rectangle, and wherein the position adjuster adjusts the position of the four light sources such that the blood vessel intersects two sides of the rectangle; and
wherein the position adjuster comprises:
a first holding unit for holding the light sources and the image capturing optical system;
a second holding unit for holding the first holding unit; and
a mounting unit for mounting the second holding unit onto the living body;
wherein the first holding unit is rotatable around an optical axis of an objective lens of the image capturing optical system when the mounting unit mounts the second holding unit onto the living body.

15. The noninvasive living body measuring apparatus of claim 14, wherein the position adjuster adjusts the position of the four light sources such that the blood vessel intersects two short sides of the rectangle.

* * * * *